United States Patent [19]

Diethelm

[11] Patent Number: 4,913,148

[45] Date of Patent: Apr. 3, 1990

[54] METHOD FOR THE TREATMENT OF HERPES SIMPLEX AND HERPES ZOSTER

[75] Inventor: Franz Diethelm, Triesen, Liechtenstein

[73] Assignee: Hepax Limited, Triesen, Liechtenstein

[21] Appl. No.: 275,634

[22] Filed: Nov. 16, 1988

Related U.S. Application Data

[63] Continuation of Ser. No. 774,446, Sep. 10, 1985, abandoned.

[30] Foreign Application Priority Data

Jul. 31, 1985 [AT] Austria ................................ 2257/85

[51] Int. Cl.$^4$ .............................................. A61N 1/32
[52] U.S. Cl. ....................................... 128/421; 128/898; 128/419 R
[58] Field of Search ................... 128/419 R, 420, 421, 128/422

[56] References Cited

U.S. PATENT DOCUMENTS

| | | | |
|---|---|---|---|
| 2,477,084 | 7/1949 | Rehman | 128/420 |
| 2,498,882 | 2/1950 | Fuzzell et al. | 128/421 |
| 3,518,996 | 7/1970 | Cortina | 128/422 |
| 3,794,022 | 2/1974 | Nawracaj et al. | 128/422 |
| 3,881,495 | 5/1975 | Pannozzo et al. | 128/422 |
| 3,911,930 | 10/1975 | Haglors et al. | 128/422 |
| 3,983,881 | 10/1976 | Wickham | 128/421 |
| 4,014,347 | 3/1977 | Halleck et al. | 128/422 |
| 4,019,510 | 4/1977 | Ellis | 128/421 |
| 4,084,595 | 4/1978 | Miller | 128/422 |
| 4,088,141 | 5/1978 | Niemi | 128/421 |
| 4,140,133 | 2/1979 | Kastrubin et al. | 128/421 |
| 4,155,366 | 5/1979 | Di Mucci | 128/421 |
| 4,177,819 | 12/1979 | Kofsky et al. | 128/422 |
| 4,181,128 | 1/1980 | Swartz | 128/362 |
| 4,233,986 | 11/1980 | Tannenbaum | 128/421 |
| 4,266,532 | 5/1981 | Ryaby et al. | 128/421 |
| 4,561,851 | 12/1985 | Ferreira et al. | 128/421 |

FOREIGN PATENT DOCUMENTS

| | | | |
|---|---|---|---|
| 2342082 | 9/1977 | France | 128/421 |
| 782815 | 11/1980 | U.S.S.R. | 128/421 |
| 793582 | 1/1981 | U.S.S.R. | 128/421 |
| 799755 | 1/1981 | U.S.S.R. | 128/421 |
| 2041752 | 9/1980 | United Kingdom | 128/421 |
| 8501213 | 3/1985 | World Int. Prop. O. | 128/421 |

OTHER PUBLICATIONS

"'Tonus 1' Apparatus for Treatment with Diadynamic Currents" by E. Sukonkina et al.; Biomed Engr., vol. 7, No. 5, pp. 323-326, Sep.-Oct. 1973.

"'Tonus 2' Portable Apparatus for Diadynamic Current Therapy" by E. Sukonkina et al.; Biomed. Engr., vol. 12, No. 2, pp. 114-117, Mar.-Apr. 1978.

Primary Examiner—William E. Kamm
Assistant Examiner—David Shay
Attorney, Agent, or Firm—Watson, Cole, Grindle & Watson

[57] ABSTRACT

A method for the treatment, by accelerating the healing process, of acute herpes simplex and acute herpes zoster, and by the reduction of post-herpetic neuralgia, subsequent to determining a dermatone on a body, which dermatome includes an area affected by herpes and which comprises a corresponding segment nerve. Two conducting electrodes are applied to the surface of the dermatome including an anode directly on the spiral ganglion of the most proximal portion of the corresponding nerve, and a cathode on the distal part of the dermatome. Electric current having a constant frequency of about 30 Hz and in the shape of monopolar pulses of an approximately square wave-form having a duration of about 0.2 msec. is applied to the electrodes. The current intensity is adjusted in corresponding with the respective skin resistance.

8 Claims, 5 Drawing Sheets

METHOD FOR THE TREATMENT OF HERPES SIMPLEX AND HERPES ZOSTER

This application is a continuation, of application Ser. No. 774,446, filed Sept. 10, 1985 now abandoned.

BACKGROUND OF THE INVENTION

This invention relates to a method for the treatment of herpes simplex and herpes zoster.

In the following description the term herpes, unless specified more precisely, will stand for all virus diseases of the skin and mucous membranes resulting from infection with the herpes simplex virus (herpes simplex) and the varicella virus (herpes zoster), herpes simplex being caused by two different types of virus affecting skin and genital mucosa, respectively.

DESCRIPTION OF THE PRIOR ART

In the case of herpes simplex conventional medical treatment is mostly symptomatic, generally protracted and unrewarding, especially for recurrent forms of the disease. There is a widespread use of virostatic ointments and solutions which must be applied over a period of several weeks. Besides, desiccating and antiseptic preparations are recommended for the affected areas of the skin.

For herpes zoster there is likewise no satisfactory therapy available. Although pain is treated symptomatically by administration of analgesics, the success of any causal therapy is controversial. Treatment of neuralgia is a big problem which has often been solved by prescription of psychopharmacological drugs and tranquilizers, and severance of the affected nerve paths in extreme cases.

SUMMARY OF THE INVENTION

It is an object of this invention to provide a method for the treatment of all types of herpes affections that will greatly accelerate the healing process and thus reduce potential periods of hospitalization, entailing a minimum of physical and mental strain for the patient. The number of relapses should be reduced as far as possible.

In order to achieve this objective the present method includes the following steps:
(a) The dermatome corresponding to the area affected by herpes is determined on the surface of the body.
(b) Two conducting electrodes are applied to the surface of the skin: an anode directly over the corresponding nerve, and a cathode on the other side of the same dermatome, as far away from the anode as possible. These electrodes are connected to a source of electrical current.
(c) The electrodes are supplied with current from the electrical source in the form of monopolar square wave pulses, the intensity of which being adjusted according to the skin resistance.

Thus a novel method has been developed for non-invasive treatment of all modes of herpes simplex and herpes zoster. In herpes conditions not involving any mucous membranes the transcutaneous treatment possible with this method and the special waveform used will permit the secreting skin areas to dry up between the fifth and seventh day of therapy and the efflorescences to heal between the tenth and fourteenth day of therapy, immunobiological processes probably playing a vital role. Even in herpes conditions affecting the mucous membranes the healing process may be expected to be far more rapid than with conventional therapy.

Patients with herpes conditions rarely see a doctor at the outbreak of the disease but mostly when it has reached its peak. Since most herpes conditions will cause unpleasant sensations therapy should be promptly conducted. As soon as a herpes affliction has been diagnosed the treatment described by this invention should commence. For this purpose the electrodes are applied to the affected dermatome and treatment is repeated several times a day, depending on the severity of the case and the intensity of pain. Additional administration of vitamin B is recommended.

During the first two or three days of therapy it is recommended to administer analgesics per os or per injectionem. After that period the alleviation of pain achieved by the present therapy will render superfluous any additional pain-killers. In cases of herpes zoster with affliction of the nervus ophthalmicus the visual faculty of the affected eye has been observed to remain intact. According to present knowledge and experience the method described by the invention will help to largely prevent recurrences. If there is a relapse it should be treated similarly as the initial affection. It can be expected that the second attack of the disease will be much shorter than the first.

Generally, the method of the invention provides that all types of herpes affections be treated according to the sensibility scheme, i.e., via the dermatome corresponding to the affected area, to which the electrodes are applied. During treatment current intensity (mA) should be adjusted such that the patient feels a discernible, but not painful, throbbing (pulsation) at the surface of the skin. It will often be necessary to increase current intensity after approximately five minutes so as to counteract habituation and reach initial conditions.

In step (b) of the method aforedescribed the anode is placed over the ganglion of the respective nerve.

As described in an article entitled, "Optimal Stimulation Sites for TENS Electrodes," by Jeffrey S. Mannheimer, 1980, dermatomes frequently overlap and lack distinct anatomical boundaries. Because of this overlap, it should be recognized by one having ordinary skill in this art that placement of an anode on the affected dermatome at the spinal ganglion of the corresponding nerve, as in the manner and for the purpose of the invention described herein, contemplates placement of additional anodes on the immediate ganglions of the inferior and superior dermatomes, without departing from the invention. The cathode is placed ventrally, at the distal part (i.e., away from the spinal ganglion) of the affected dermatome.

In herpes affections of the facial and cranial areas, for instance, electrical treatment is administered to the nervus trigeminus and its three branches, corresponding to the facial half affected. Depending on the area affected by herpes, the particular dermatome must be given single or multiple cathode treatment, the single anode being applied at the ganglion Gasseri (ganglion trigeminale). The cathodes are placed at the point of the affected dermatome most distant from the anode. If several dermatomes are affected within the same facial half the use of one anode and several cathodes will suffice.

In herpes affections above the girdle the proper dermatome is determined and an anode is applied such that it is located precisely over the point of exit of the corresponding spinal nerve. In a zoster condition, e.g., which has spread over two or three intercostal areas, a corresponding number of anodes may be applied, whereas the cathode is applied on the other side, i.e., the abdomen, in a homolateral position.

The method described by the invention may be applied both in acute conditions (with or without efflorescences) and in treatment of post-herpetic pain. Treatment is continued until the efflorescences have healed and pain has been stopped or alleviated considerably. In many cases it will be necessary to administer analgesics before therapy-induced analgesia has fully come into effect.

In case of a relapse therapy should set in as quickly as possible; if a relapse is anticipated within two weeks, for instance, it is recommended to administer treatment for the next 14 days consecutively, even if no symptoms (pain and/or efflorescences) can be observed during this period.

In herpes affections below the girdle—the most common condition being herpes genitalis by which both the vagina and the penis or the surrounding areas (herpes progenitalis) can be afflicted—the anode is transcutaneously applied in a paravertebral position on the right or left side of the second sacral dermatome. In the case of visible efflorescences around the genitalis the corresponding dermatomes must also be included in the treatment.

For the method described here it will be best to use electric current of an intensity of 5–100 mA. Current intensity should be regulated by the patient himself who should feel a discernible pulsation at the skin surface which should not be painful, however.

In a variant of the method described by the invention the individual square wave pulses of step (c) have a duration of 0.1 to 1 msec. In this context a time of 0.2 msec has proved best. Outside this range of pulse times therapy either will be less effective or it will induce electrolytic processes in the tissue which might cause damage at skin level and deeper.

Particularly favorable results have been achieved with a pulse frequency between 5 and 150 Hz in step (c), a frequency of 30 Hz being especially suitable for therapy. Frequencies below 5 Hz may arouse unpleasant sensations (electric shocks). It should be noted that frequencies above 180 Hz can produce motory nerve blocks.

Another proposal provides the use of two electrodes of different sizes in step (b), the smaller one serving as the anode and the bigger one as the cathode. As a rule, therapy should be administered transcutaneously with electrodes of different sizes, the anode being relatively small to achieve a sufficient density of flux lines in order to carry enough current towards the nerve. On the other hand the cathode should be relatively large in order to disperse cathodic irritation, to save the patient from unpleasant sensations or irritations.

Conventional electrodes made of synthetic materials or silicones may be used which are known from electrocardiography, for instance. The electrodes are covered with a suitably sized strip of natural resin (caraya) which is electrically conducting. After moistening them with water they are fastened to the skin. They may also be coated with a thin layer of electrode gel and attached to the skin with a strip of adhesive tape. For treatment of affections in areas of the head electrodes with circular contact surfaces are employed, with diameters of approximately 13 mm for the anode and approximately 29 mm for the cathode. The electrode serving as a cathode on the head, i.e., of approximately of 29 mm diameter may be used as an anode on the body. For better distribution of cathode irritations a cathode of a large surface area, e.g., a 120×70 mm rectangle, should be used on the body.

As regards step (c) of the method under discussion, treatment with current pulses should last for a period of 10 to 40 minutes. A treatment period of 20 minutes has proved best.

The method described by the invention may be further improved by repeating treatment every five hours and by maintaining this schedule for at least five days in succession.

As an example, reference will be made to generalized herpes therapy. The attack (the visible efflorescences) always starts with a local herpes affection which will then spread. Therapy should concentrate on the initial location (e.g., in case of herpes zoster intercostalis the electrodes are applied paravertebrally, in correspondence with the dermatomes). Treatment is administered three times a day for 20 minutes at intervals of 5 hours, and is continued until efflorescences, pain and other symptoms are on the decline.

In patients suffering from leukemia herpes affections have been observed subsequent to marrow transplants. Patients whose body defense system has been weakened by medication following transplantations, are recommended to undergo preventive herpes treatment according to the invention immediately after transplantation.

In order to achieve better effects and a more rapid response to the treatment the patient should be protected from all kinds of stress during therapy.

Equipment for treatment of herpes simplex and herpes zoster according to the method of the invention comprises an electric current source delivering monopolar pulses, preferably of a square waveform, to two or more electrodes which are connected to the current source by conducting wires and are attached to the surface of the patient's skin, current intensity of these pulses ranging from 5 to 100 mA, their duration from 0.1 to 1 msec and their frequency from 5 to 150 Hz. The efficiency of the method and equipment described herein is demonstrated by a comparison of the therapy of herpes zoster according to the invention versus lassical therapy. If a zoster condition is treated by the present method, periods of hospitalization may be reduced by 50%, and post-herpetic neuralgia may be eliminated or largely reduced. After an average of 8 days the patient is anticipated to be free from pain, a marked alleviation of pain will be felt after 3 days. Within two days of treatment the condition of the skin will have improved, i.e., the secreting areas will dry up and local therapy will no longer be necessary. If a conventional therapy is used which is almost exclusively invasive, treatment may take as long as six months with hospitalized patients. No influence on recurrencies has been observed. Apart from the unpredictable (long-term) after-effects of medication, various intolerances may occur. Due to the compact design of the equipment described by the invention patients with less severe herpes conditions may be treated out of the hospital or even at home with rented equipment. Post-herpetic pain after classical herpes treatment often necessitates neurosurgery. In such cases treatment according to the present invention again is recommended as it will relieve the patient from pain and eliminate the need for surgery. Conventional therapy often requires risotomy, but experience has shown that about half of the patients will continue to be in pain.

Basically it may be assumed that the surprising success of the method of the invention is due to favorable immuno-biological processes in the human body.

In carrying out the invention the current source is configured as a microprocessor fed from a power supply, which controls a constant current generator the output of which is connected to a current meter, and which in turn is fed back to the microprocessor which is provided with a keyboard for the input of treatment data such as current intensity and duration of treatment, and with a display unit for display and control of this information. The equipment under discussion is powered by 8 NiCd batteries of 1.2V and 600 mA each. Via the keyboard the current intensity required for treatment can be increased or decreased step by step. The constant current generator which is controlled by the microprocessor, produces and supplies the current pulses required for therapy, current intensity having been preset via the keyboard. The current meter connected with the output of the constant current generator delivers its readings to the microprocessor checking and controlling the data entered which are displayed on a two-digit liquid crystal display (alternative display of current intensity and duration of treatment).

A preferred variant provides that the microprocessor be connected via a data line and an address line with a memory unit storing the pulse data, preferably frequency and pulse duration. For this purpose a ROM unit may be used which will read into the microprocessor all data necessary for pulse generation, such as frequency, pulse duration, pulse shape.

According to the invention it will be of advantage to provide the microprocessor with a, preferably acoustic, indicator/warning unit for indication of the end of treatment and for error messages. This indicator unit, e.g., a piezo buzzer integrated into the device, or a small loudspeaker, is primarily used for indicating the end of a 20 minutes treatment session. At the same time the unit may have warning functions, for instance, it may indicate an interruption of current flow due to poor electrode contact, or a voltage drop in the power supply of the equipment. It is also possible to provide visual display and warning units, e.g., blinking LEDs.

According to a particularly favorable form of the invention the current meter has a peak-hold circuit measuring current peaks; if a certain preset level is exceeded the device will switch off automatically. The peak-hold circuit is primarily added for reasons of safety, protecting the patient from unpleasant electric shocks which may result from static charge or from differences in potential between the equipment and other objects with which the patient is in contact or additional facilities required for therapy.

In a further variant power is supplied by a set of rechargeable batteries whose voltage may be measured by means of a charge control unit which will activate a LED and will automatically interrupt treatment in case of a voltage drop. This is a further safety facility which may also be incorporated into the microprocessor, showing the actual time spent on treatment on the display if a treatment session is interrupted due to a voltage drop.

A further development of the invention may provide that an additional memory unit be connected to the microprocessor which will store treatment data of the patient, preferably the number and duration of treatment sessions. Thus specific data of the patient may be retrieved prior to each treatment session, which will permit better control of the treatment schedule.

DESCRIPTION OF THE DRAWINGS

Following is a more detailed description of the invention as illustrated by the accompanying drawings, in which

In FIG. 1 C2–C8 denote the cervical, T1–T12 the thoracic, L1–L5 the lumbar, S1–S5 the sacral dermatomes. Typical electrode positions in herpes therapy according to the invention are:

Herpes genitalis: anode A on dermatome S2, right or left; cathode A' on the other side, abdomen, homolateral position.

Herpes zoster: anode B on dermatome T3, right or left; cathode B' on the other side, thorax, homolateral position.

Herpes progenitalis: anode C on dermatome L1, right or left; cathode C' on the other side, thorax or abdomen, homolateral position.

Herpes analis: anode D on dermatome S5, alternating between right and left; cathode D' on the other side, across the symphysis, median position.

Figure 1:
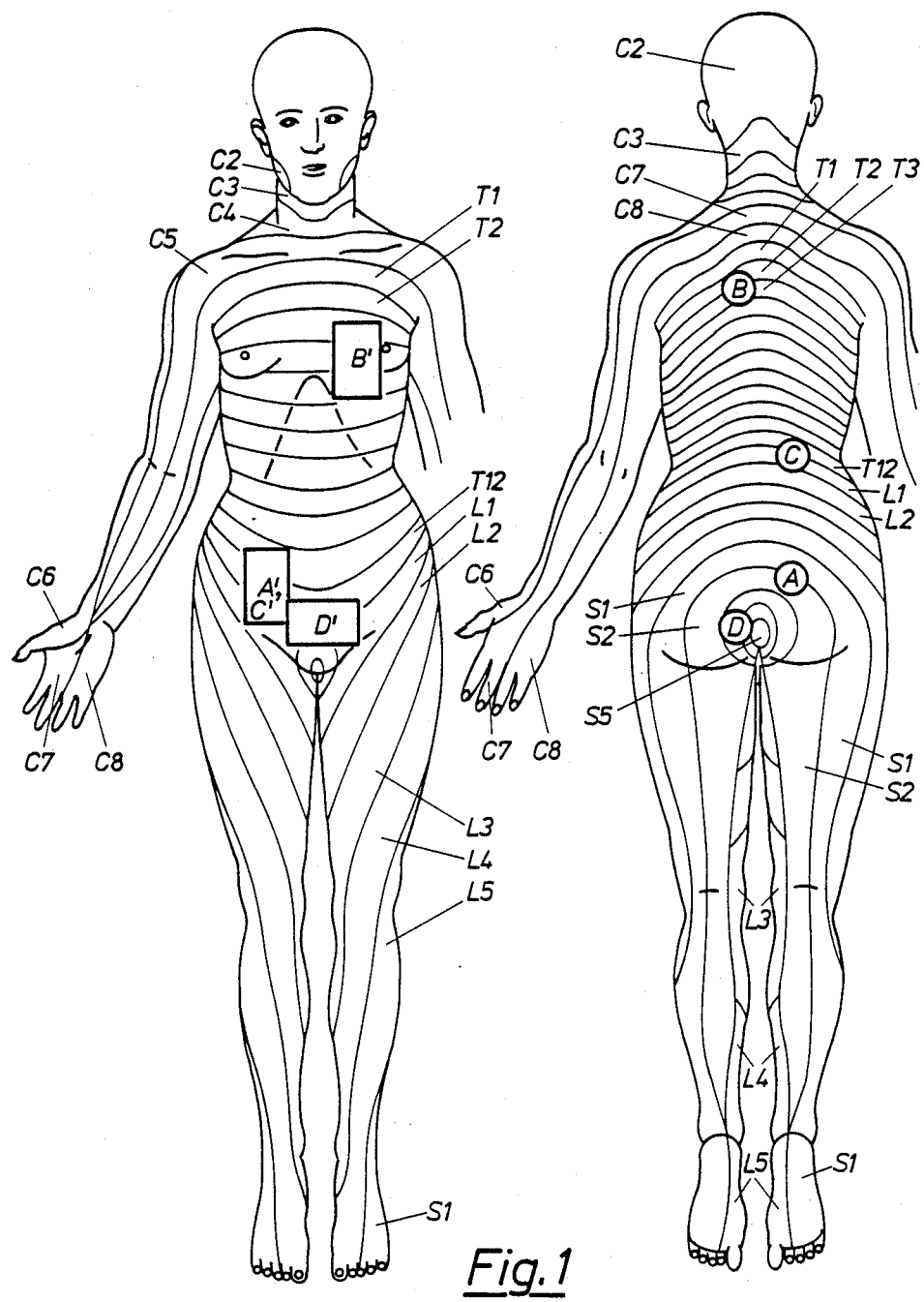
FIG. 1 illustrates possible electrode placements in herpes therapy according to the invention.
Figure 2:
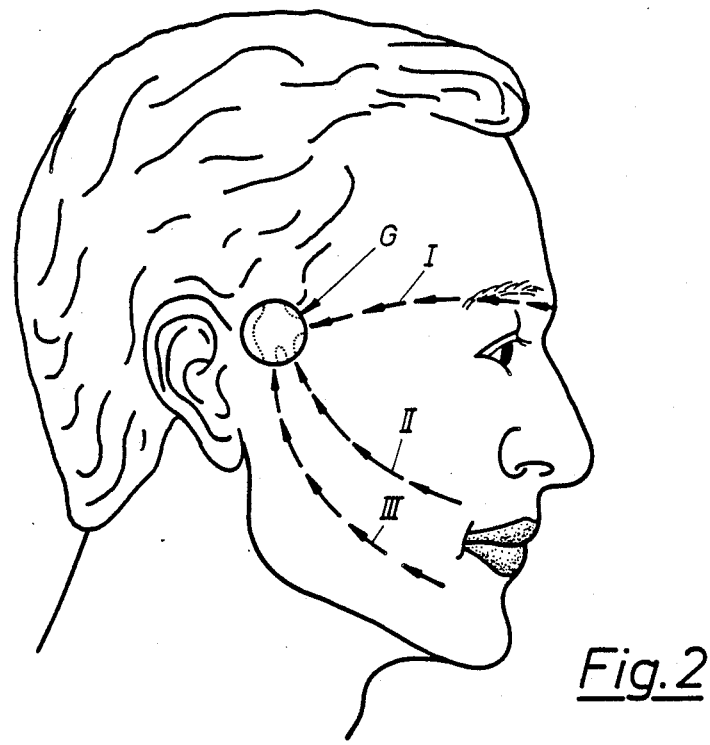
FIG. 2 illustrates the point on the surface of the head from which three nerve branches depart.

In FIG. 2 the point on the surface of the head beneath which the ganglion trigeminale (Gasseri) is situated, is marked G. This ganglion is the point of departure for the three branches of the nervus trigeminus, i.e., nervus ophtalmicus I, nervus maxillaris II, nervus mandibularis III.

Figure 3:
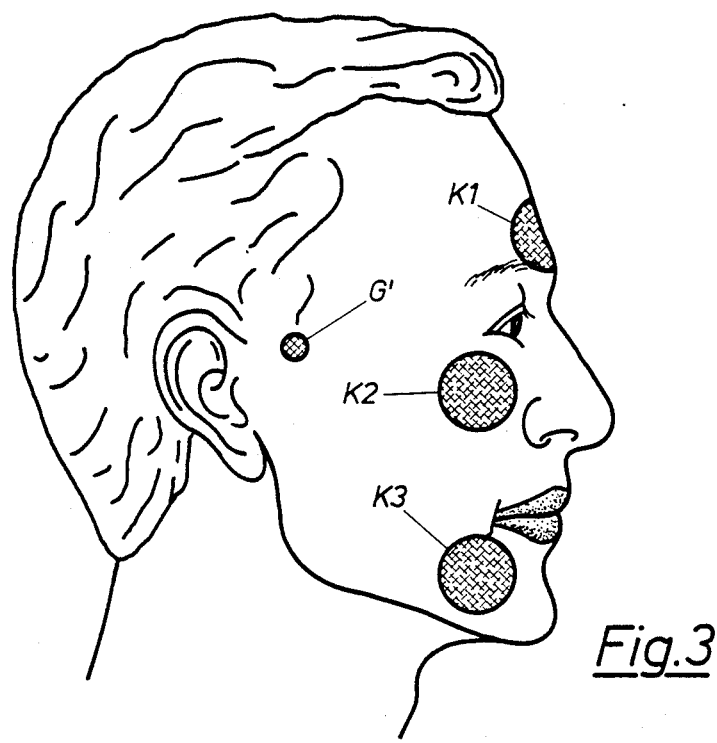
FIG. 3 illustrates electrode placement in the facial area according to the invention.

If one or several of these nerve branches are affected by herpes the electrodes are applied as shown in FIG. 3. In this case the anode G' whose contact surface has a diameter of 13 mm approximately, is placed over the ganglion Gasseri. The cathodes K1 to K3 with diameters of 29 mm approximately, are at the positions indicated in FIG. 3.

Figure 4:
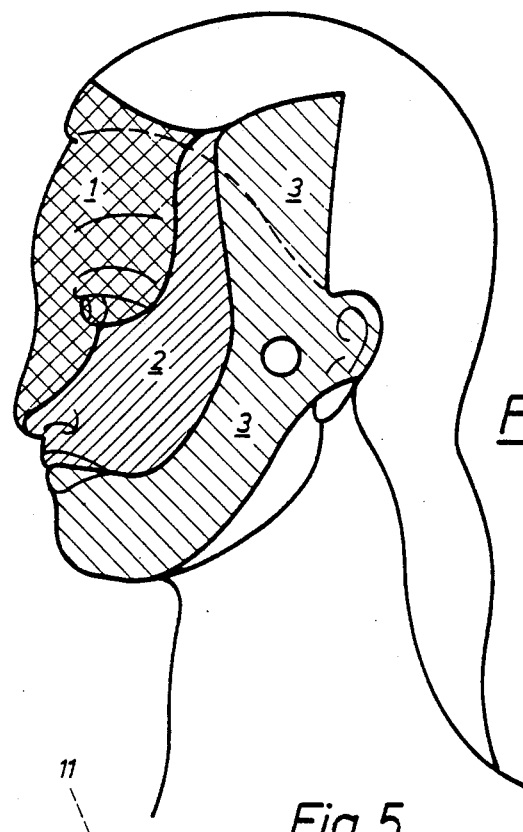
FIG. 4 illustrates the dermatomes covered by the three nerve branches of FIG. 2.

In FIG. 4 the dermatomes covered by the three branches of nervus trigeminus have the numbers 1 to 3. For instance, in a herpes labialis affection of the upper and/or lower lip, the corresponding dermatome(s) (second and/or third) should be treated. The anode G' should be placed at the ganglion Gasseri and the cathode(s) at the electrode positions K2 and/ or K3 (FIG. 3). If dermatome 1 is also affected another cathode should be placed in front of the respective eyebrow. Affections of the face may easily be treated by means of one anode and three cathodes. The same dermatomes are treated in affections of the mucous membranes in the cavity of the mouth.

Figure 5:
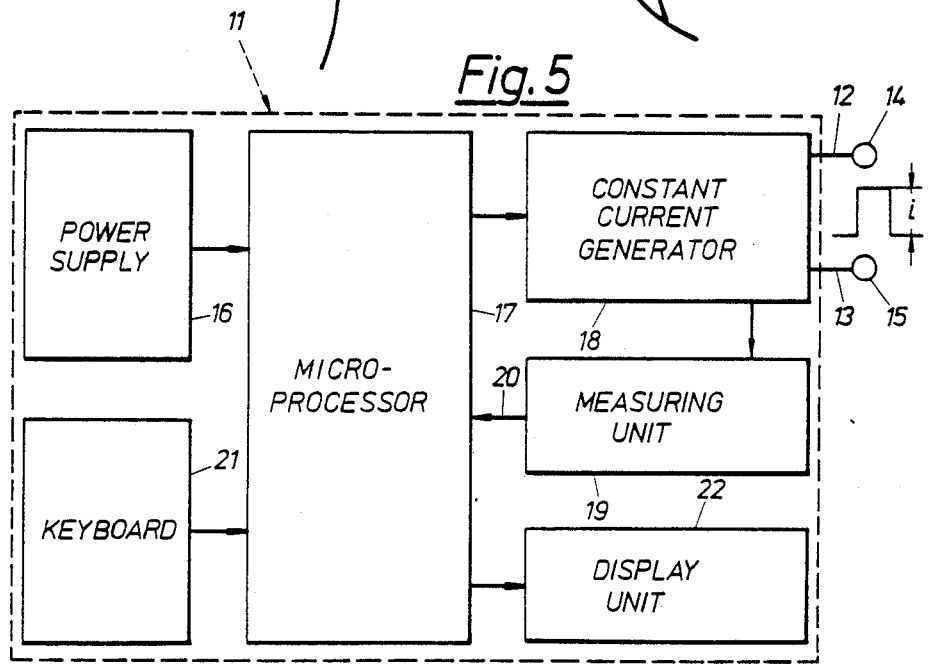
FIG. 5 the block diagram of a device for the treatment of herpes simplex and herpes zoster as specified by the invention, FIG. 6 the diagram of another equipment variant in herpes therapy, FIG. 7 a diagram of the monopolar current pulses.

FIG. 5 is a diagram of a current source 11 which is connected to the electrodes 14, 15 to be applied at the patient's body via wires 12, 13. The microprocessor 17 is the key unit used for control of the entire device, i.e., for pulse control, reading in of commands entered via the keyboard 21, and control of the display unit 22. Power supply 16 of the device is configured either as a set of batteries or as a mains supply unit. The microprocessor 17 also controls a constant current generator 18 which will deliver to the patient the current pulses i required for treatment via electrodes 14, 15. A unit 19 is used to measure the output current, the obtained values being digitized and fed to the microprocessor 17 via a feedback loop 20.

Figure 6:
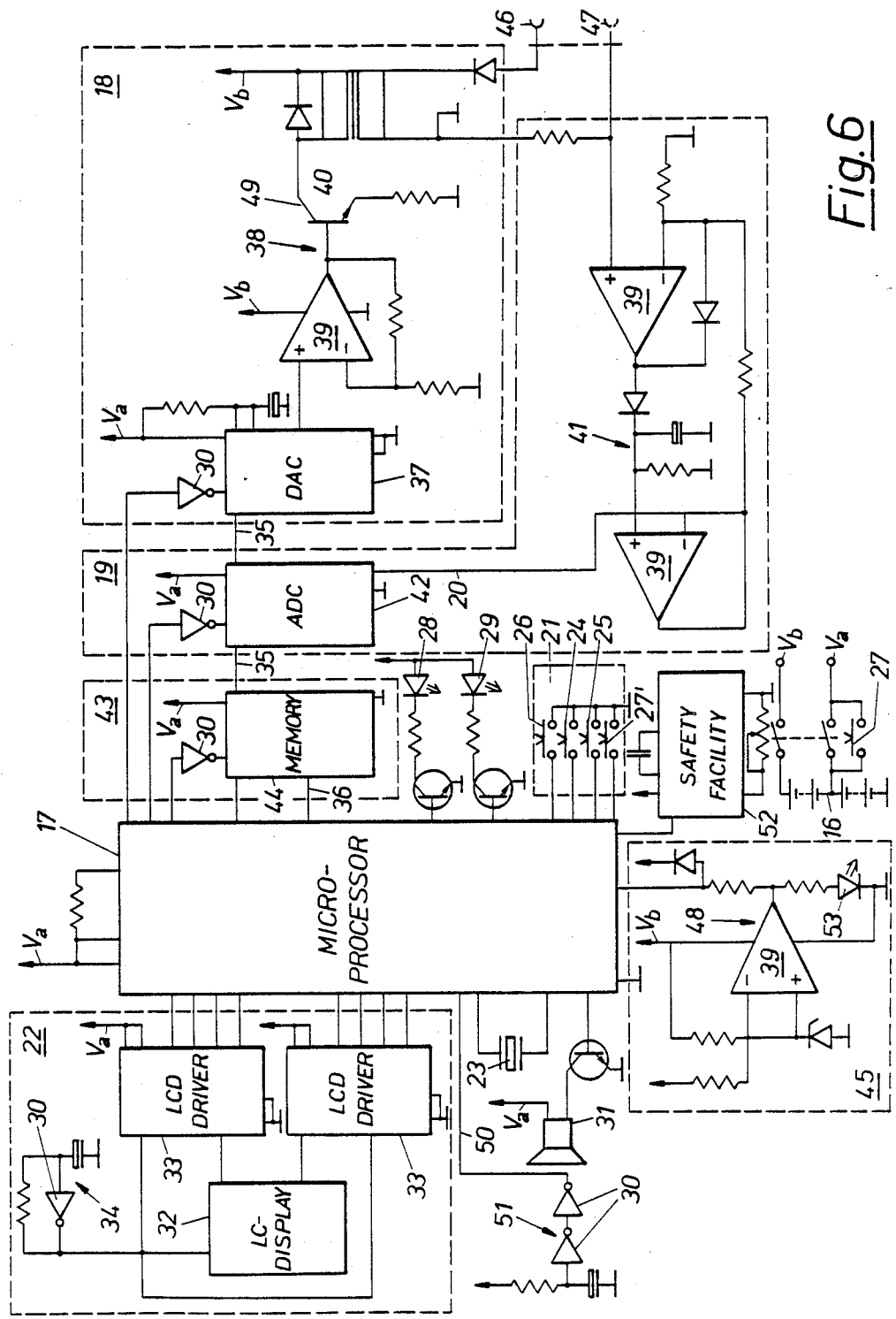

In FIG. 6 the boxes indicated by broken lines contain the electronic components and correspond to the boxes of FIG. 5, carrying identical reference numbers. After the device has been switched on by means of a touch button 27 a supply voltage of Va=9.6 V or Vb=4.8 V is applied to the supply lines of the individual components. The microprocessor 17, for instance a unit of the type R65 0 1Q from Rockwell, is fed by its supply line and is operated at a clock frequency (quartz 23) of 4 megacycles. Via keys 24 and 25 of the keyboard 21 the current intensity during treatment may be increased or diminished. Key 26 switches the display unit to display of treatment duration, touch button 27' is used for switching off the device. The LEDs 28, 29 indicate the operational state of the display unit (current measurement vs. time measurement). Due to the circuit 51 (power-up-reset) at the reset input 50 of the microprocessor 17 the device will start operating only when the microprocessor is running at its preset clock frequency. Components 30 of the circuit are digital inverters.

The device also has an acoustic indicator/warning facility 31 fulfilling various functions, such as acoustic indication of the end of a treatment session, an interruption of the flow of current due to loose electrodes, etc., or internal flaws of the device. If there is no current flow through the electrodes, the warning unit is actuated and the current is switched off, the device itself remaining operational.

The display unit 22 of the device comprises an LC display 32, e.g., an Epson LD-H 7980 AZ, which is driven by two LCD drivers 33 (74 HC 4543 from National). Decoding of BCD into 7-segment code is also performed here. An oscillator 34 will generate a square wave voltage of 60 Hz approx., supplying the LC display unit 32.

Via the digital data line 35 a digital-to-analog converter 37 (Ferranti ZN 428) is connected to the microprocessor 17, converting the digital current control data into analog form and controlling the end stage of the constant current generator 38 with an operational amplifier 39, a power transistor 49 (Darlington MPSU 45) and a pulse transformer 40 whose output circuit is connected with the electrode terminals 46, 47 and which is capable of transmitting steep pulse slopes with a minimum of distortion.

The current meter 19 has a peak-hold circuit 41 for recognition of possible current peaks and for continuous current measurement, and an analog-to-digital converter 42 that is connected with the microprocessor 17 via the digital data line 35, e.g., an ADC 0804 unit from National, for converting the analog readings into digital form and transmitting them to the microprocessor. Components 39 of the circuit 41 are operational amplifiers (LM 2902 from National).

The equipment also comprises a storage unit 43 with a programmed memory 44, e.g., an MBM 27C32 A from Fujitsu, which is connected with the microprocessor 17 via the digital data line 35 and the address line 36. This ROM unit contains all parameters for pulse control, such as frequency, pulse duration, etc.

The use of an additional memory unit would permit storage of patient-specific treatment parameters which would simplify multiple treatment activities.

The equipment also comprises a charge control unit 45 with a comparator circuit 48 for recognition of voltage drops. In case of a voltage drop the LED 53 is activated. The charge control unit 45 is connected to the microprocessor 17 and will trigger an acoustic warning signal in case of a voltage drop, following which the device is automatically switched off.

A unit 52 (74HC123 from National) with a watch-dog circuit is a safety facility monitoring and controlling the microprocessor 17. Any interruption or deviation of the program flow will cause a switch-off of the equipment.

Figure 7:
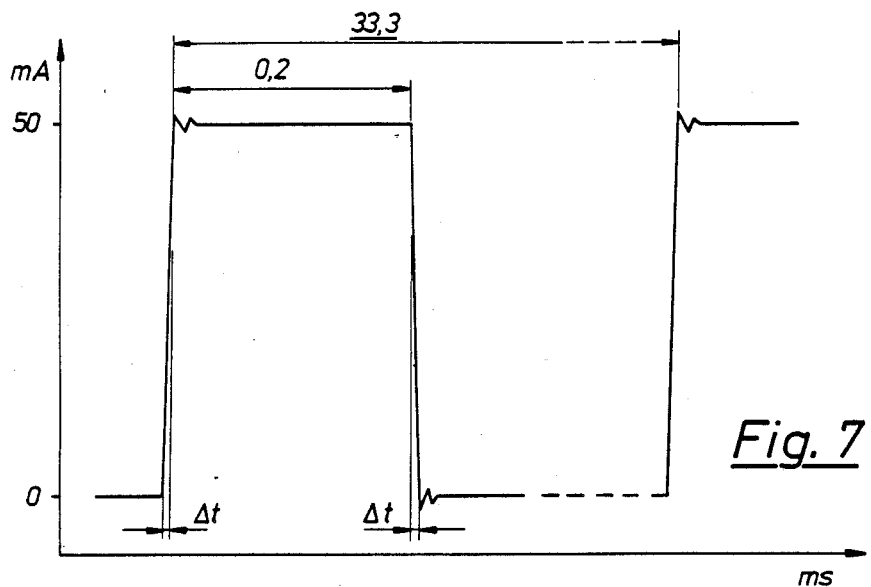

By means of the electrodes 14, 15 to be applied at the affected dermatome, monopolar current pulses of an approximately square wave-form (cf. FIG. 7) are transmitted to the patient. Pulse duration is 0.2 msec and current intensity 50 mA, for example. The latter may be varied from 0 to 65 mA, and is adjusted and maintained constant in correspondence with the skin resistance of the patient. Pulse frequency is 30 Hz. Pulse slopes should be as steep as possible (small $\Delta t$), with a minimum of trailing and overshoot.

I claim:

1. A method for the treatment, by accelerating the healing process, of acute herpes simplex and acute herpes zoster, and by the reduction of post-herpetic neuralgia, subsequent to determining a dermatome on a body, said dermatome including an area affected by herpes and comprising a corresponding sensory segmental nerve, comprising:
    applying two conducting electrodes to the surface of said dermatome including an anode directly on the spinal ganglion of the most proximal portion of said corresponding nerve, and a cathode on the distal part of said dermatome;
    supplying said two conducting electrodes with current from a source of electrical current having a constant frequency of about 30 Hz and in the shape of monopolar pulses of an approximately square wave-form having a duration of about 0.2 msec., and adjusting the current intensity in accordance with the respective skin resistance, whereby the healing process of herpes affections is accelerated, and occurrences of herpes and post-herpetic neuralgia are reduced.

2. A method according to claim 1, wherein in said step of supplying, electric current of an intensity of 5-100 mA is supplied.

3. A method according to claim 1, further comprising substantially protecting the patient from stress.

4. A method according to claim 1, wherein in said step of applying the applied two electrodes have different sizes, the smaller one serving as said anode and the larger one as said cathode.

5. A method according to claim 1, wherein in said step of supplying current said current pulses are applied for a period of 10-40 minutes.

6. A method according to claim 5, wherein in said step of supplying current said pulses are applied for a period of substantially 20 minutes.

7. A method according to claim 6, wherein in said step of supplying current the application of said pulses is repeated substantially every 5 hours.

8. A method according to claim 7, wherein in said step of supplying current the application of said pulses is continued for at least 5 days in succession.

* * * * *